United States Patent [19]

Baglioni

[11] Patent Number: 4,571,399
[45] Date of Patent: Feb. 18, 1986

[54] 7-(1-METHYL-5-P-METHYLBENZOYLPYR-ROLE-2-ACETAMIDOETHYL)-THEOPHYLLINE WITH ANTI-PLATELET AGGREGANT AND BRONCHOLYTIC ACTIVITY

[75] Inventor: Alessandro Baglioni, Rome, Italy

[73] Assignee: Medosan Industrie Biochimiche Riunite S.p.A., Rome, Italy

[21] Appl. No.: 634,494

[22] Filed: Jul. 26, 1984

[30] Foreign Application Priority Data

Jul. 29, 1983 [IT] Italy ................. 48782 A/83

[51] Int. Cl.⁴ ................. A61K 31/52; C07D 473/08
[52] U.S. Cl. ................. 514/265; 544/269; 548/539
[58] Field of Search ............. 544/269; 514/264, 265; 548/539

[56] References Cited

U.S. PATENT DOCUMENTS 3,015,658  1/1962  Jucker et al. ............ 544/269
3,565,896  2/1971  Ghielmetti et al. .......... 544/269
3,998,953  12/1976  Konz et al. ............... 544/269
4,060,617  11/1977  Credner et al. ............ 514/265
4,465,843  8/1984  del Valle ................. 548/539
4,528,382  7/1985  Mills .................... 548/539

Primary Examiner—Donald G. Daus
Assistant Examiner—Stephen M. Kapner
Attorney, Agent, or Firm—Cushman, Darby & Cushman

[57] ABSTRACT

A new therapeutic agent with anti-platelet aggregant activity is described, with the chemical formula of 7-(1-methyl-5-p-methylbenzoylpyrrole-2-acetamidoethyl)-theophylline:

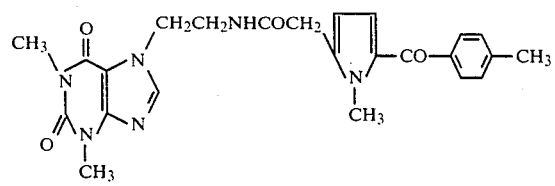

3 Claims, No Drawings

7-(1-METHYL-5-P-METHYLBENZOYLPYRROLE-2-ACETAMIDOETHYL)-THEOPHYLLINE WITH ANTI-PLATELET AGGREGANT AND BRONCHOLYTIC ACTIVITY

BACKGROUND OF THE INVENTION

1. Field of the Invention

The present invention refers to a new therapeutic agent with the chemical structure of 7-(1-methyl-5-p-methylbenzoylpyrrole-2-acetamidoethyl)theophylline (1)

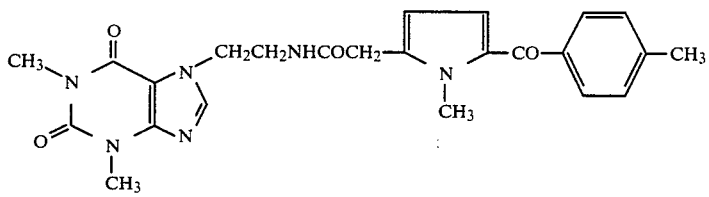

2. Description of the Prior Art

This amide is an example of an amide derivative of 7-(2-aminoethyl)theophylline which combines in a single molecule the theophylline component with 1-methyl-5-p-methylbenzoylpyrrole-2-acetic acid, a known antinflammatory agent known as tolmetin.

SUMMARY OF THE INVENTION

The newly prepared molecule shows pronounced therapeutically useful anti-platelet aggregant activity, but has the low antinflammatory and analgesic effects predicted for this type of molecule due to the presence of the chemical component known as tolmetin. However, it shows good broncholytic activity comparable to that of theophylline.

DESCRIPTION OF THE PREFERRED EMBODIMENT 7-(1-Methyl-5-p-methylbenzoylpyrrole-2-acetamidoethyl)theophylline (1) was prepared by amidation of 1-methyl-5-p-methylbenzoylpyrrole-2-acetic acid (2)

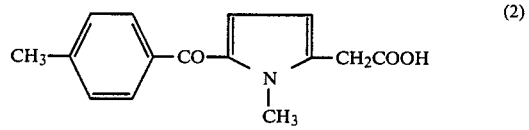

with 7-(2-aminoethyl)theophylline (3)

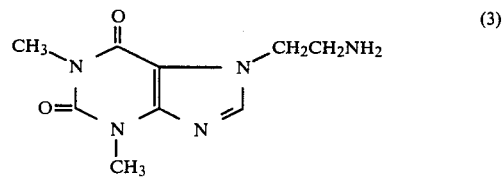

in the presence of a stoichiometric amount of N,N'-carbonyldiimidazol as condensing agent according to the scheme reported hereinafter.

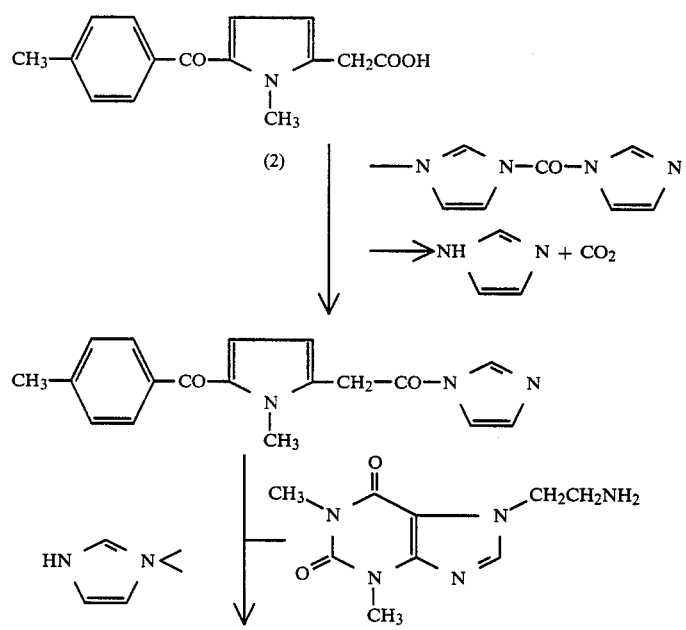

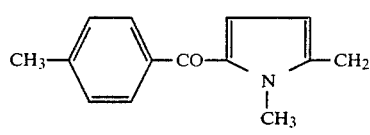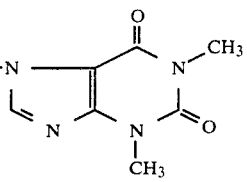

(1)

7-(1-Methyl-5-p-methylbenzoylpyrrole-2-acetamido-ethyl)theophylline (1) was prepared as follows:

A solution of 1-Methyl-5-p-methylbenzoylpyrrole-2-acetic acid (1.29 g; 5 mmol) in dichloromethane (50 ml) is added dropwise to a solution of N,N'-carbonyl-diimidazol (1.22 g; 7.5 mmol) in the same solvent (50 ml). The resulting solution is stirred at room temperature for an hour, and then treated dropwise over 20 minutes with a solution of 7-(2-aminoethyl)theophylline (1.12 g; 5 mmol) in dichloromethane (50 ml). The resulting mixture is stirred overnight at room temperature, filtered, and placed in a separatory funnel. The organic solution is washed with 5% NaOH (2×35 ml), and then with water until neutral. After drying over anhydrous sodium sulfate, the solution is filtered and the solvent is evaporated under vacuum. 1,9 g of crude amide (82.6%) are isolated as a white solid with m.p. 195°–197° C. Crystallization from a 1:1 mixture of ethyl alcohol and ethyl acetate affords 1.3 g of 7-(1-Methyl-5-p-methyl-benzoylpyrrole-2-acetamidoethyl)theophylline with m.p. 199°–200° C.

Analysis for $C_{24}H_{26}N_6O_4$ %calc.: C 62.32; H 5.67; N 18.17 %found: C 62.61, H 5.93; N 17.89 corresponding to the compound:

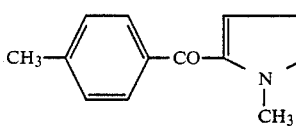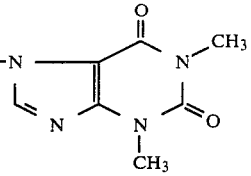

with the following chemical and physical properties:
Formula: $C_{24}H_{26}N_6O_4$
Molecular weight: 462.56
Melting point: 199°–200° C.
Solubility: soluble in dichloromethane, N,N'-dimethylformamide

PHARMACOLOGICAL PROPERTIES

The experiments performed with 7-(1-Methyl-5-p-methylbenzoylpyrrole-2-acetamidoethyl)theophylline, compound (1), show that it has pharmacological properties therapeutically useful in certain pathological conditions.

In in vivo studies, the compound was administered orally and/or parenterally in a 0.5% suspension of carboxymethylcellulose in pH neutral physiological saline. In in vitro studies, on the other hand, it was used as a fine dispersion in pH neutral physiological saline.

The test compound showed anti-platelet aggregant activity plus good broncholytic action. These pharmacotherapeutic effects were obtained using dosages and administration routes that caused no significant toxic effects.

The anti-platelet aggregant activity was compared with that of aspirin; the broncholytic activity, with that of theophylline.

Anti-platelet aggregant activity

This activity was studied in vitro following Born's method (G. W. R. Born, Nature, 194, 937 (1962)) and inducing platelet aggregation with ADP.

Platelet rich plasma was prepared by centrifuging 9 parts rat blood with 1 part 3.13% trisodium citrate solution, for 10 minutes at 2000 rpm. For the aggregation test, 0.2 ml of platelet rich plasma was mixed with a NaCl solution (0.9%) to which the test substance was added up to a final volume of 0.6 ml. Incubation was fixed at 3 minutes at 27° C. After aggregation was induced with ADP, the course of the aggregation was monitored continuously with an Elvi 840 Aggregometer (Elvi Logos-Milan).

The antiaggregant effects were determined by the difference in the light transmission of the sample with respect to that of the ADP control. The test compound was compared with aspirin, which has known antiplatelet aggregant activity (H. J. Weiss et al., J. Clin. Inv., 47, 2169 (1968); Platelet Aggregation and Drugs, edited by L. Caprino and E. C. Rossi, page 235, Academic Press (London), 1974).

Table 1 reports the inhibition of platelet aggregation with various doses of the compounds tested at a constant ADP concentration. Table II gives the results obtained by varying the ADP concentration.

TABLE I

In vitro anti-platelet aggregant activity of 7-(1-methyl-5-p-methylbenzoylpyrrole-2-acetamidoethyl)-theophylline - compound (1).

| Inducer | Compound | Dose | Inhibition % |
|---|---|---|---|
| ADP 7,08 μmol/l | (1) | 1 γ/ml | 12 |
| ADP 7,08 μmol/l | " | 5 γ/ml | 59 |
| ADP 7,08 μmol/l | " | 10 γ/ml | 90 |
| ADP 7,08 μmol/l | Aspirin | 1 γ/ml | 15 |
| ADP 7,08 μmol/l | " | 5 γ/ml | 60 |
| ADP 7,08 μmol/l | " | 10 γ/ml | 100 |

TABLE II

In vitro anti-platelet aggregant activity of 7-(1-methyl-5-p-methylbenzoylpyrrole-2-acetamidoethyl) theophylline - compound (1).

| Inducer | Compound | Dose | Inhibition % |
|---|---|---|---|
| ADP 5 μmol/l | (1) | 1 γ/ml | 21 |
| ADP 5 μmol/l | Aspirin | 1 γ/ml | 19 |

TABLE II-continued

In vitro anti-platelet aggregant activity of 7-(1-methyl-5-p-methylbenzoylpyrrole-2-acetamidoethyl) theophylline - compound (1).

| Inducer | Compound | Dose | Inhibition % |
|---|---|---|---|
| ADP 2 μmol/l | (1) | 1 γ/ml | 30 |
| ADP 2 μmol/l | Aspirin | 1 γ/ml | 29 |

Broncholytic activity

The experiments were performed in vitro on guinea pig tracheal chains according to Akasu's method (A. Akasu, *Int. Pharmacodyn.*, 122, 201 (1959)), using histamine as the bronchoconstrictor agent.

The test compound was left in contact with the tissue for three minutes. A spasmogenic dose ($10^{-4}M$) of histamine was then administered; the histamine was left in contact for five minutes. The control compound was theophylline. The ratio between equally active histamine doses was calculated before and after treatment. The percent response, that is the above value multiplied by 100, was inversely proportional to the dose.

The results are reported in table III.

TABLE III

Antagonist action of 7-(1-methyl-5-p-methylbenzoylpyrrole-2-acetamidoethyl) theophylline - compound (1).

| Compound | Concentration (g/ml) | Number of tests | Response % ± exp. error |
|---|---|---|---|
| Theophylline | $1 \times 10^{-5}$ | 4 | 58 ± 9 |
| " | $2 \times 10^{-5}$ | 4 | 25 ± 8 |
| " | $5 \times 10^{-5}$ | 4 | 9 ± 2 |
| (1) | $1 \times 10^{-5}$ | 4 | 61 ± 10 |
| " | $2 \times 10^{-5}$ | 4 | 27 ± 7 |
| " | $5 \times 10^{-5}$ | 4 | 10 ± 3 |

Toxicity

The acute toxicity of compound (1) was determined in two animal species: male Swiss albino mice and male Wistar rats. The animals were 26±2 g and 130 g in weight, respectively, and were treated orally and intraperitoneally.

Table IV reports the $LD_{50}$ values (mg/kg) for the test compound, plus the literature values for aspirin and theophylline (Drug dosage in laboratory animals, C. D. Barnes and L. G. Eltherington; University of California Press, 1973).

TABLE IV

Acute toxocity of 7-(1-methyl-5-p-methyl-benzoyl-pyrrol-2-acetoamidoethyl) theophylline - compound (1)

| Compound | Animal species | $DL_{50}$ (mg/kg) os | i.p. |
|---|---|---|---|
| (1) | mouse | 1400 | 970 |
| " | rat | 1200 | 900 |
| Aspirin | mouse | 1100 | 495 |
| " | rat | 1500 | 500 |
| Theophylline | mouse | 200 s.c. | minimum lethal dose |
| " | rat | 325 s.c. | minimum lethal dose |

The data reported in tables I–IV show the pharmacotherapeutic effect of 7-(1-methyl-5-p-methylbenzoyl-pyrrole-2-acetamidoethyl)theophylline at the doses tested and in comparison with the control compounds.

The compound seems to possess a high therapeutic index: in fact the acute toxicity values are several orders of magnitude higher than those used for pharmacologically active doses. For the doses and administration routes used and indicated in the experiments described above, there was no mortality caused over the long or short term, and there were no apparent signs of toxic effects.

The examples reported for anti-platelet aggregant, anti-inflammatory and broncholytic activity, in comparison to substances with known activity, witness the therapeutic interest of the pharmaceutical composition according to the present invention.

The patients in need of an antiplatelet aggregant and broncholytic pharmaceutical composition will be orally or parenterally administered a therapeutically effective amount of 7-(1-methyl-5-p-methylbenzoyl-pyrrole-2-acetoamidoethyl)theophylline.

In practice, the compound is orally or parenterally administered in any of the usual pharmaceutical forms which are prepared by conventional procedures well-known to those persons skilled in the pharmaceutical technology. These forms include solid and liquid unit dosage forms such as tablets, capsules, suppositories, solutions, syrups and the like as well as injectable forms, such as sterile solutions for ampoules and phials.

I claim:

1. 7-(1-Methyl-5-p-methylbenzoylpyrrole-2-acetamidoethyl)theophylline of formula:

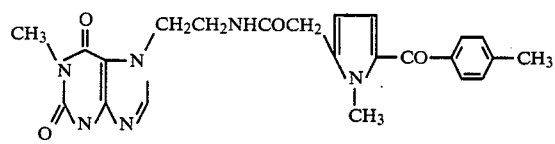

2. A pharmaceutical composition containing as an essential anti-aggregant and broncholytic active ingredient a therapeutically effective amount of 7-(1-Methyl-5-p-methylbenzoylpyrrole-2-acetamidoethyl)theophylline and a pharmaceutically compatible carrier or diluent.

3. The method of using the compound of claim 1 as an anti-platelet aggregant agent by administering an anti-platelet aggregant effective amount to an animal in need thereof.

* * * * *